(12) United States Patent
Honda (10) Patent No.: US 11,022,740 B2
(45) Date of Patent: Jun. 1, 2021

(54) ILLUMINATION UNIT FOR ENDOSCOPE AND ENDOSCOPE

(71) Applicant: OLYMPUS CORPORATION, Tokyo (JP)

(72) Inventor: Kazuki Honda, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/788,729

(22) Filed: Feb. 12, 2020

(65) Prior Publication Data
US 2020/0174174 A1 Jun. 4, 2020

Related U.S. Application Data

(63) Continuation of application No. PCT/JP2018/031837, filed on Aug. 28, 2018.

(30) Foreign Application Priority Data

Sep. 11, 2017 (JP) .............................. JP2017-174017

(51) Int. Cl.
*F21V 8/00* (2006.01)
*A61B 1/06* (2006.01)
(Continued)

(52) U.S. Cl.
CPC ........ *G02B 6/0008* (2013.01); *A61B 1/00096* (2013.01); *A61B 1/0607* (2013.01);
(Continued)

(58) Field of Classification Search
CPC ............... G02B 6/0008; G02B 23/243; G02B 23/2469; A61B 1/0607; A61B 1/0676; A61B 1/0669; A61B 1/0661; A61B 1/07
See application file for complete search history.

(56) References Cited

U.S. PATENT DOCUMENTS

2008/0242935 A1* 10/2008 Inoue ................. A61B 1/00165
600/176
2011/0282148 A1* 11/2011 Kase .................. A61B 1/00177
600/113
(Continued)

FOREIGN PATENT DOCUMENTS

EP 2586358 A1 5/2013
EP 2742851 A1 6/2014
(Continued)

OTHER PUBLICATIONS

International Search Report dated Nov. 13, 2018 issued in PCT/JP2018/031837.

*Primary Examiner* — William N Harris
(74) *Attorney, Agent, or Firm* — Scully, Scott, Murphy & Presser, P.C.

(57) ABSTRACT

An illumination unit for endoscope is provided with: a light guiding layer, an illumination lens, light guides and a positioning member; and the positioning member is provided with: a barrel body on which arrangement grooves are formed, the barrel body being configured to perform inward positioning of the light guides in the radial direction by distal end sides of the light guides being arranged in the arrangement grooves; and a cylindrical member configured to perform outward positioning of the light guides in the radial direction by covering an outer circumference of the barrel body in an intersection direction to block the distal end sides of the light guides arranged in the arrangement grooves, between the cylindrical member and the barrel body in the intersection direction.

10 Claims, 8 Drawing Sheets

(51) Int. Cl.
*G02B 23/24* (2006.01)
*A61B 1/00* (2006.01)
*A61B 1/07* (2006.01)

(52) U.S. Cl.
CPC .......... *A61B 1/0669* (2013.01); *A61B 1/0676* (2013.01); *G02B 23/2423* (2013.01); *G02B 23/2469* (2013.01); *A61B 1/07* (2013.01)

(56) References Cited

U.S. PATENT DOCUMENTS

| | | |
|---|---|---|
| 2012/0190990 A1 | 7/2012 | Ohzawa et al. |
| 2013/0258081 A1 | 10/2013 | Akui et al. |
| 2014/0347878 A1 | 11/2014 | Honda et al. |
| 2016/0103312 A1 | 4/2016 | Furuta |
| 2017/0055817 A1* | 3/2017 | Dybiec .............. A61B 1/00096 |
| 2017/0059848 A1* | 3/2017 | Haraguchi ............. A61B 1/051 |
| 2018/0256014 A1* | 9/2018 | Shinji .................. A61B 1/0615 |
| 2019/0313891 A1* | 10/2019 | Oka ..................... A61B 1/0623 |

FOREIGN PATENT DOCUMENTS

| | | |
|---|---|---|
| EP | 2815691 A1 | 12/2014 |
| EP | 3020321 A1 | 5/2016 |
| JP | S62-040415 A | 2/1987 |
| JP | 2009-207529 A | 9/2009 |
| JP | 5274719 B2 | 8/2013 |
| JP | 2015-016021 A | 1/2015 |
| JP | 2017-099485 A | 6/2017 |
| WO | WO2011/162342 A1 | 12/2011 |
| WO | WO2013/021739 A1 | 2/2013 |
| WO | WO2014/073426 A1 | 5/2014 |

* cited by examiner

$Ra1 \leqq Rb1$
$Ra2 \geqq Rb2$

FIG. 5

$Ra1 \leqq Rb1$
$Ra2 \geqq Rb2$

ILLUMINATION UNIT FOR ENDOSCOPE AND ENDOSCOPE

CROSS REFERENCE TO RELATED APPLICATION

This application is a continuation application of PCT/JP2018/031837 filed on Aug. 28, 2018 and claims benefit of Japanese Application No. 2017-174017 filed in Japan on Sep. 11, 2017, the entire contents of which are incorporated herein by this reference.

BACKGROUND OF THE INVENTION

1. Field of the Invention

The present invention relates to an illumination unit for endoscope provided on a distal end side of an insertion portion of an endoscope in a longitudinal axis direction and provided with a light emitting member configured to diffuse illumination light in an intersection direction intersecting the longitudinal axis direction, and light guiding members configured to guide the illumination light to the light emitting member, and the endoscope.

2. Description of the Related Art

Recently, endoscopes have been widely used in a medical field and an industrial field. Endoscopes make it possible to observe an inside of a subject by inserting an elongated insertion portion into the subject.

Note that, as such an endoscope, a front-view type endoscope provided with an observation lens and an illumination lens on a distal end face of a distal end portion provided on a distal end side of an insertion portion and a side-view type endoscope provided with the observation lens and the illumination lens on a part of an outer circumferential face of the distal end portion of the insertion portion are well known.

Further, recently, endoscopes capable of observing not only a field of view of an area in a longitudinal axis direction of the insertion portion but also a field of view of an area including an intersection direction intersecting the longitudinal axis direction at the same time to expand an observation range in a subject have been well known. Such an endoscope is disclosed in Japanese Patent No. 5274719.

Note that a front area ahead of the distal end face of the insertion portion is given as a specific example of the area in the longitudinal axis direction of the insertion portion, and a surrounding-direction area located in a radial direction of the distal end portion substantially orthogonal to the longitudinal axis direction, for example, located around an outer circumferential face of the distal end portion is given as a specific example of the area including the intersection direction.

The endoscope disclosed in Japanese Patent No. 5274719 has a projecting portion configured with a first projecting portion and a second projecting portion columnarly projecting forward from the distal end face of the distal end portion of the insertion portion of the endoscope.

A front observation lens, which is a first observation optical system, is provided in the first projecting portion, facing a distal end face of the first projecting portion.

Furthermore, in the first projecting portion, a surrounding observation lens, which is a second observation optical system having a partial annular shape excluding the second projecting portion along an outer circumferential face of the first projecting portion, is provided behind the front observation lens.

Furthermore, in the distal end portion, a lens group is located behind the surrounding observation lens, and an image pickup portion such as a CCD is located at a light condensing position of the lens group.

A configuration is made in which an image of an object located ahead of the distal end face of the first projecting portion is acquired as a front object image by the front observation lens, and light incident onto the front observation lens passes through the surrounding observation lens and is formed on the image pickup portion by the rear lens group.

A configuration is made in which an image of a subject located in a surrounding direction, which is a direction of intersection with the first projecting portion, is acquired by the surrounding observation lens as a side object image, and light incident onto the surrounding observation lens is formed on the image pickup portion by the rear lens group after being reflected in the lens a plurality of times.

Note that, on a display portion, the front object image is displayed in a substantially circular shape, and the side object image is displayed in a partial annular shape excluding an area blocked by the second projecting portion, for example, in a substantially C shape, surrounding an outer circumference of the front object image.

Thereby, an operator can observe not only a front field of view but also a side field of view in the surrounding direction at the same time from the display portion. In other words, it is possible to perform observation of a wide range in a subject.

Furthermore, a front illumination lens configured to illuminate a subject located in front is provided on a distal end face of the second projecting portion.

On the outer circumferential face of the first projecting portion, a side illumination lens having a partial annular shape excluding the second projecting portion along the outer circumferential face and configured to illuminate a subject located in the surrounding direction is provided at a position adjacent to the surrounding observation lens.

Here, the side illumination lens disclosed in Japanese Patent No. 5274719 is provided at a position facing respective distal end faces of a plurality of light guides having a circular section, which are light guiding members provided in the insertion portion, and configured to diffuse light incident from the respective distal end faces in the surrounding direction.

In Japanese Patent Application Laid-Open Publication No. 2015-16021, a section on a distal end side of each light guide facing a side illumination lens is formed in an ellipse, a polygon, a fan shape or the like. The side illumination lens is configured with a light guiding layer which is a first layer located facing a distal end face of each light guide and configured to diffuse incident illumination light inside, and a diffusing layer which is a second layer located on an outer layer of the light guiding layer and configured to cause the illumination light diffused in the light guiding layer to be diffused in the surrounding direction. Therefore, such a configuration of an illumination unit for endoscope is disclosed that illumination light is uniformly radiated in the surrounding direction without irregularity, and increase in a diameter of a distal end portion is prevented by the section on the distal end side being formed in a shape other than a circle.

SUMMARY OF THE INVENTION

An illumination unit for endoscope according to an aspect of the present invention is provided with: a light emitting member provided on a distal end side of an insertion portion of an endoscope in a longitudinal axis direction, the light emitting member including a first layer which includes an end face provided in an intersection direction intersecting the longitudinal axis direction and an outer circumference portion provided in a circumferential direction around a longitudinal axis, the first layer being configured to diffuse illumination light incident onto the end face inside, and the second layer being arranged on an outer layer side in the intersection direction with respect to the outer circumference portion of the first layer and configured to cause the illumination light diffused by the first layer to be diffused in the intersection direction; light guiding members configured to guide the illumination light to the light emitting member, each of the light guiding members including a proximal end face onto which the illumination light from a light source is incident, and a distal end face facing the end face of the first layer to cause the illumination light to be incident onto the first layer and having a shape including an oval shape obtained by extending a circle in the circumferential direction; and a positioning member configured to position the light emitting member and the light guiding members in a radial direction of the insertion portion in the intersection direction so that all the distal end faces of the light guiding members face the end face of the first layer, and the positioning member includes a barrel body on which such arrangement grooves are formed in the longitudinal axis direction that the positioning member performs inward positioning of the light guiding members in the radial direction by distal end sides of the light guiding members in the longitudinal axis direction being arranged in the arrangement grooves, and a cylindrical member configured to perform outward positioning of the light guiding members in the radial direction by covering an outer circumference of the barrel body in the intersection direction to block the distal end sides of the light guiding members arranged in the arrangement grooves, between the cylindrical member and the barrel body in the intersection direction.

An endoscope according to the present invention is provided with the illumination unit for endoscope.

DETAILED DESCRIPTION OF THE PREFERRED EMBODIMENT

An embodiment of the present invention will be described below with reference to drawings. Note that it should be noticed that the drawings are schematic, and a relationship between thickness and width of each member, a thickness ratio among respective members and the like are different from actual ones, and it goes without saying that, among the drawings, portions having a different mutual dimensional relationship or ratio are included.

Figure 1:
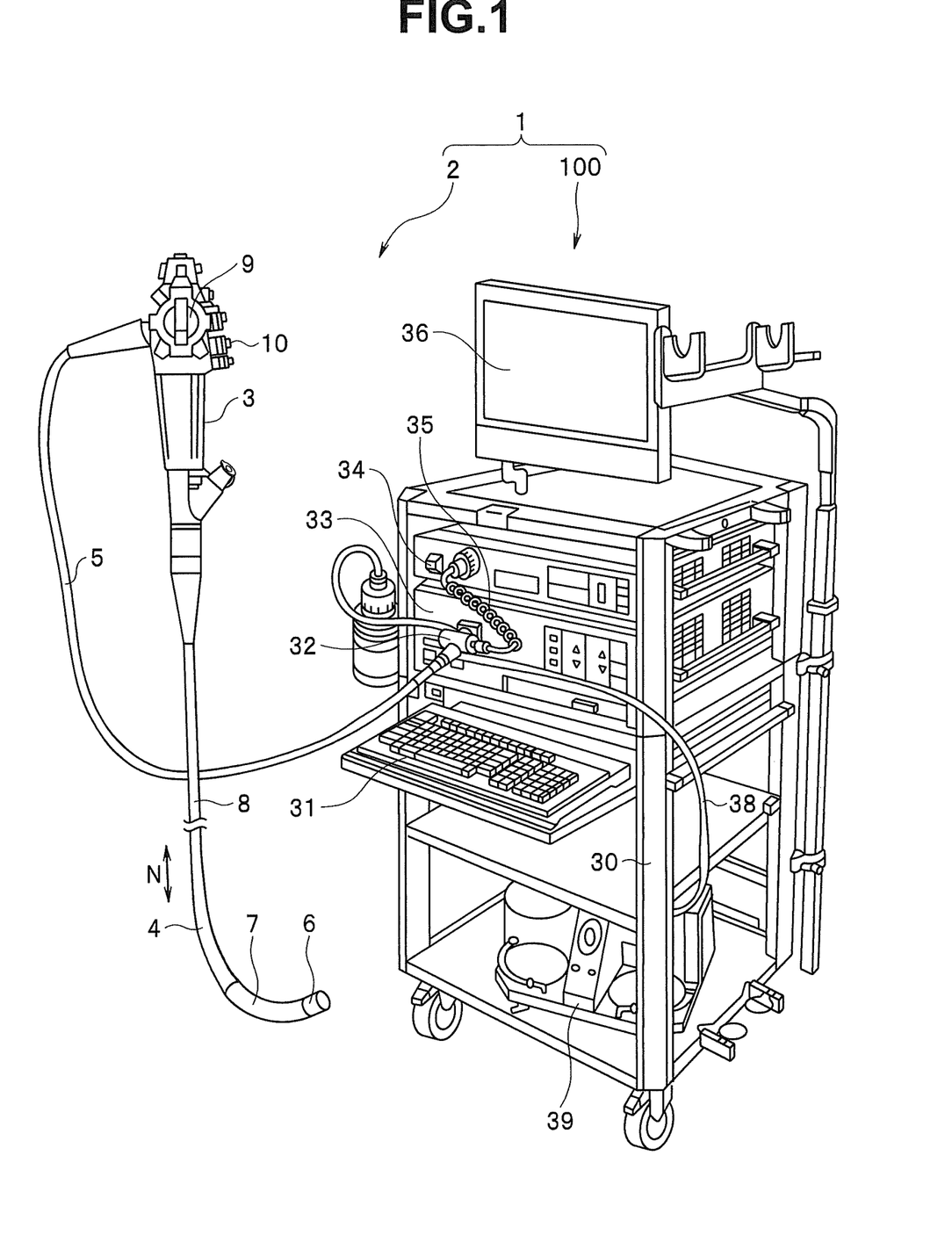
FIG. 1 is a perspective view schematically showing an example of an endoscope apparatus configured with an endoscope provided with an illumination unit for endoscope showing the present embodiment, and a peripheral apparatus.

FIG. 1 is a perspective view schematically showing an example of an endoscope apparatus configured with an endoscope provided with an illumination unit for endoscope showing the present embodiment, and a peripheral apparatus.

As shown in FIG. 1, an endoscope apparatus 1 is configured with an endoscope 2 and a peripheral apparatus 100.

The endoscope 2 is provided with an insertion portion 4 to be inserted into a subject and an operation portion 3 connectedly provided on a proximal end of the insertion portion 4.

The endoscope 2 is provided with a universal cord 5 extended from the operation portion 3, and a connector 32 provided on an extension end of the universal cord 5.

The peripheral apparatus 100 is provided with a keyboard 31, a light source apparatus 33, a video processor 34, a connection cable 35 configured to electrically connect the light source apparatus 33 and the video processor 34, a monitor 36 and a suction pump 39, which are placed on a stand 30.

The endoscope 2 and the peripheral apparatus 100 having such configurations are connected to each other via the connector 32.

The connector 32 is connected with the light source apparatus 33 of the peripheral apparatus 100, for example. The connector 32 is provided with a pipe sleeve (not shown) with which a proximal end of a suction channel (not shown) provided in the insertion portion 4, the operation portion 3 and the universal cord 5 is connected. A tube 38 extended from the suction pump 39 is connected with the pipe sleeve.

The connector 32 is provided with a light guide pipe sleeve constituting proximal ends of light guides 90, 90', 90" and 190 (see FIGS. 3, 5 and 12) inserted in the insertion portion 4, the operation portion 3 and the universal cord 5, and an electrical contact portion and the like.

Furthermore, the operation portion 3 of the endoscope 2 is provided with a bending operation knob 9, a suction button 10 and the like.

The suction pump 39 sucks outside air via an opening of the suction button 10, the suction channel and the tube 38 after being driven. When the opening of the suction button 10 is covered by the operator, the suction pump 39 sucks liquid in a subject via a suction port 17 (see FIG. 2), the suction channel and the tube 38.

The insertion portion 4 of the endoscope 2 is elongatedly configured in a longitudinal axis direction N with a distal end portion 6 located on a distal end side of the insertion portion 4, a bending portion 7 connectedly provided on a proximal end of the distal end portion 6 and a flexible tube portion 8 connectedly provided on a proximal end of the bending portion 7.

The bending portion 7 is bending-operated, for example, in four directions of up, down, left and right by the bending operation knob 9 provided on the operation portion 3.

Figure 2:
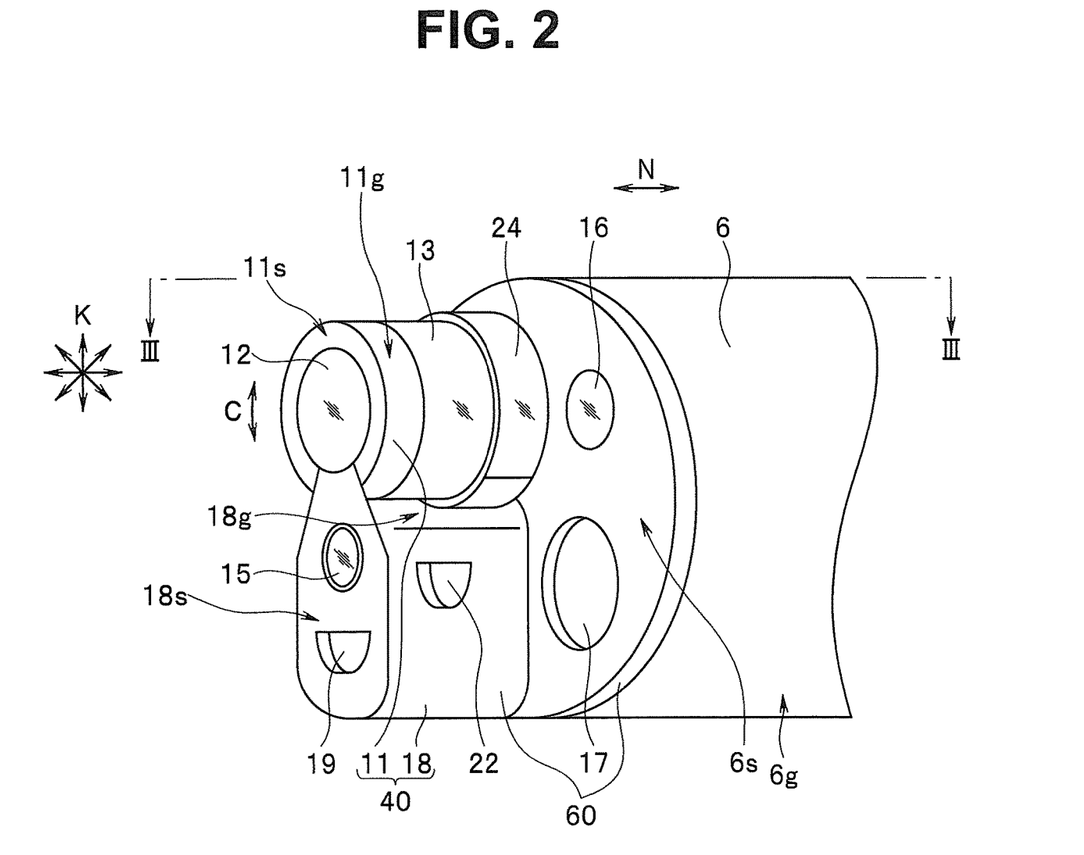
FIG. 2 is a partial perspective view enlargingly showing a distal end portion in FIG. 1.
Figure 3:
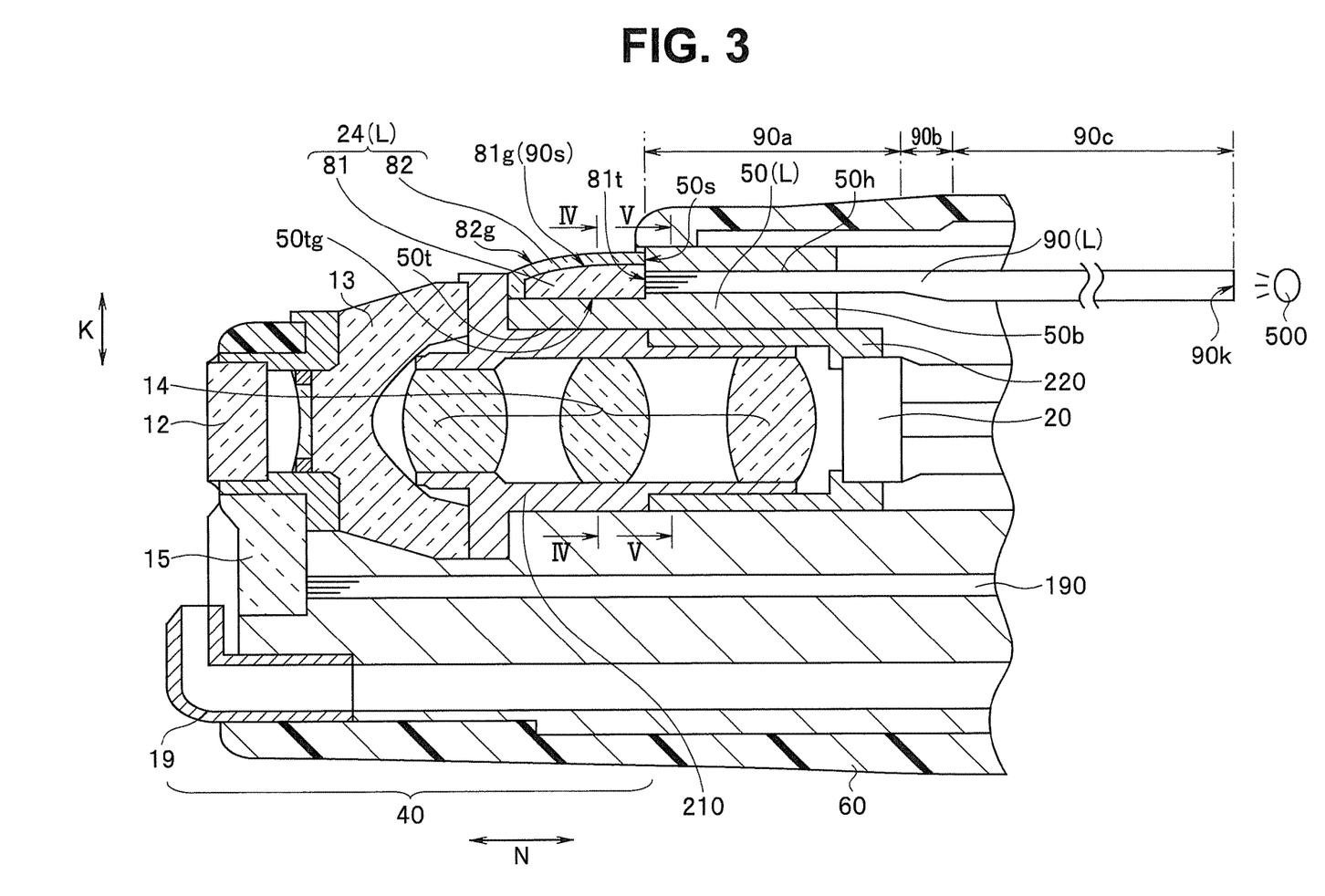
FIG. 3 is a diagram schematically showing a section along a line in FIG. 2, together with a light source.

Next, a configuration of the distal end portion 6 will be described with the use of FIGS. 2 to 10. FIG. 2 is a partial perspective view enlargingly showing the distal end portion in FIG. 1; and FIG. 3 is a diagram schematically showing a section along a line in FIG. 2, together with a light source.

Figure 4:
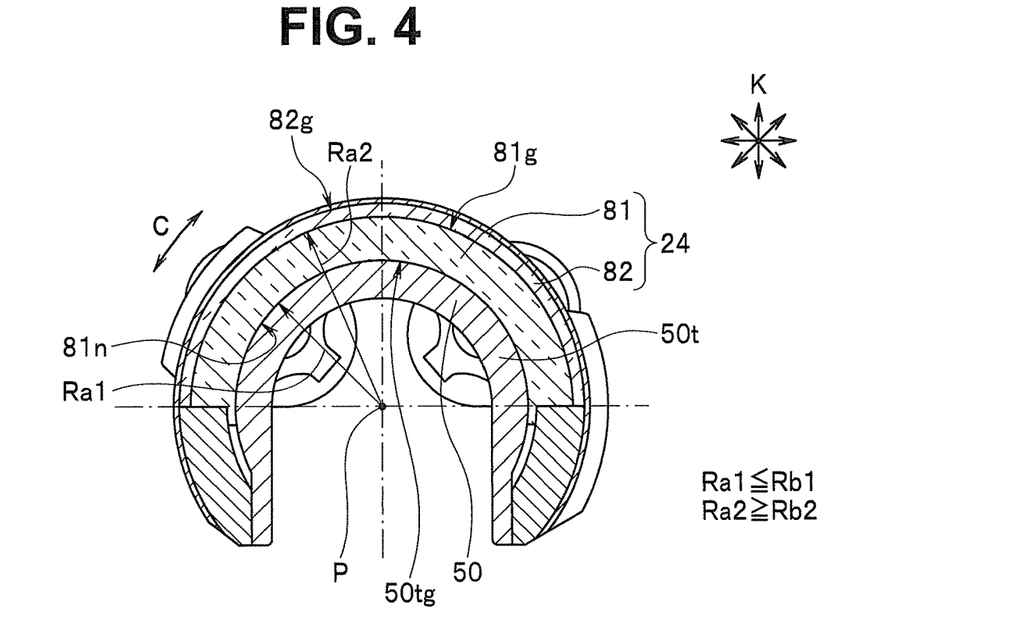
FIG. 4 is a cross-sectional view of a barrel body and a light emitting member along a IV-IV line in FIG. 3.
Figure 5:
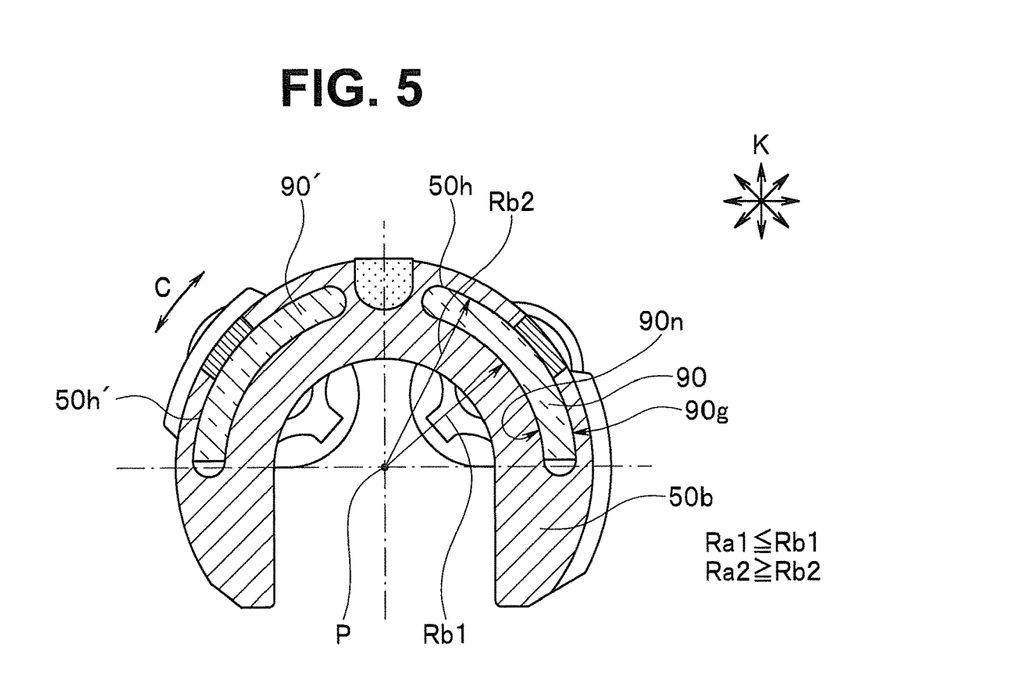
FIG. 5 is a cross-sectional view of the barrel body and a light guiding member along a V-V line in FIG. 3.
Figure 6:
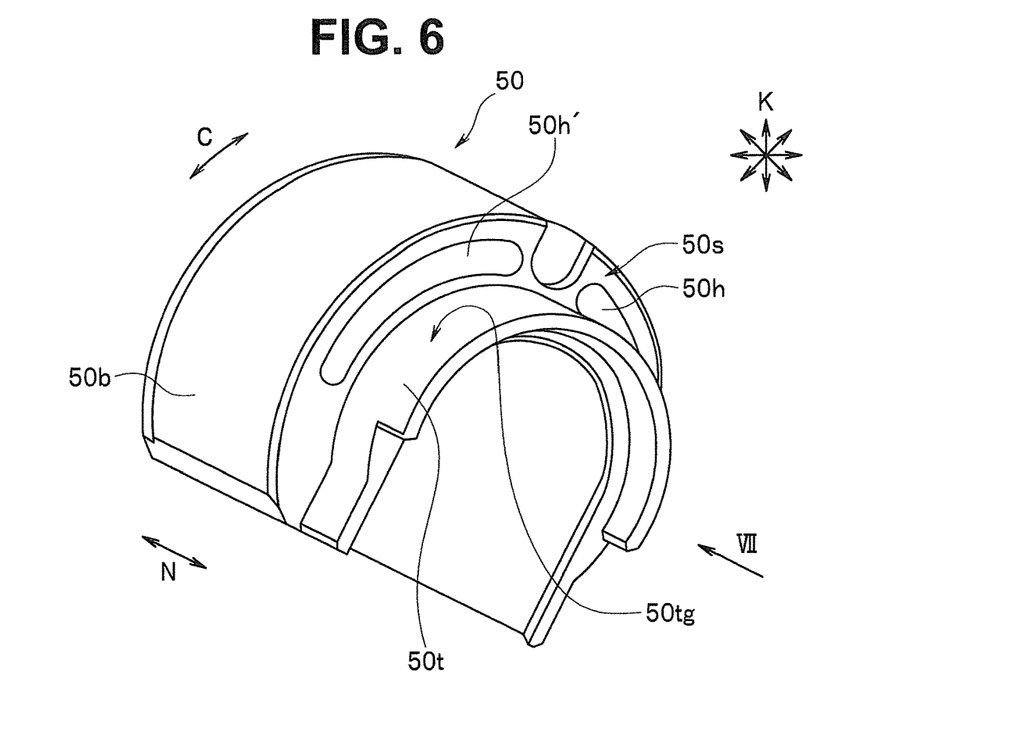
FIG. 6 is a perspective view enlargingly showing the barrel body in FIG. 3.
Figure 7:
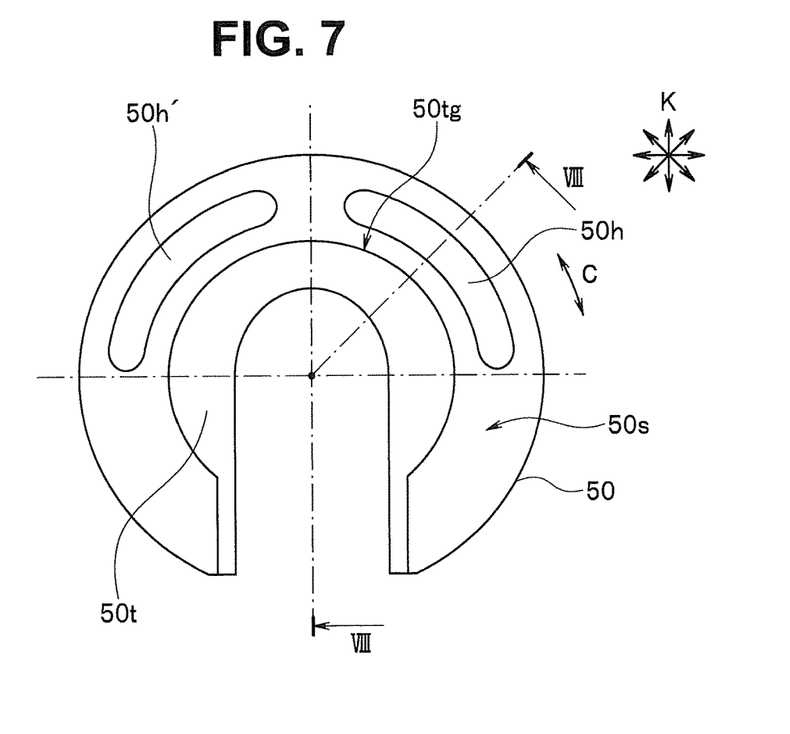
FIG. 7 is a plan view when the barrel body in FIG. 6 is seen in a VII direction in FIG. 6.
Figure 8:
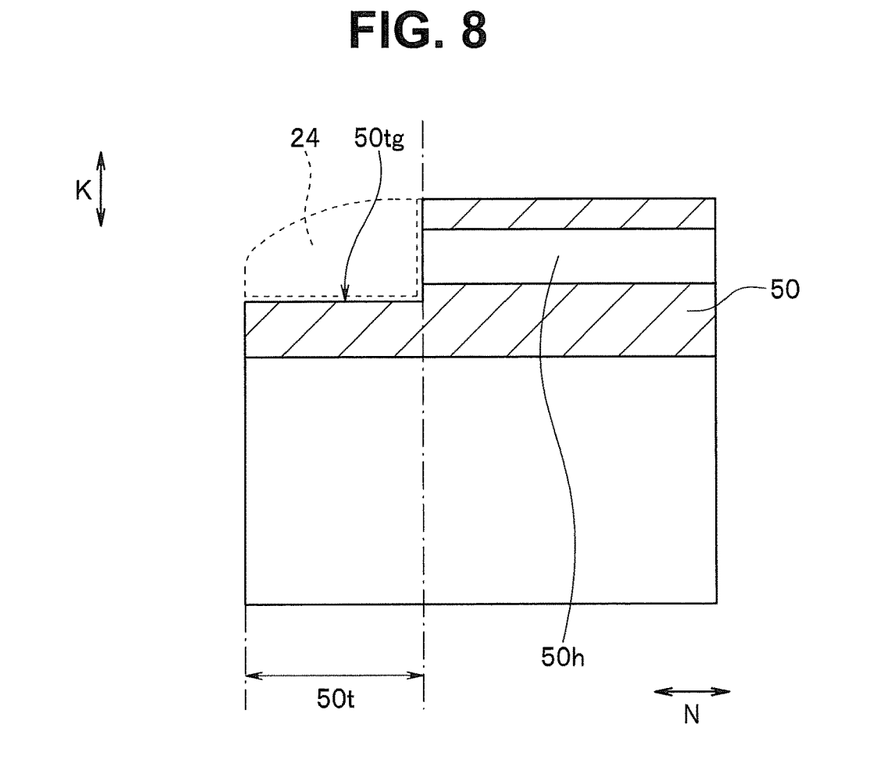
FIG. 8 is a cross-sectional view of the barrel body along a VIII-VIII line in FIG. 7.

FIG. 4 is a cross-sectional view of a barrel body and a light emitting member along a IV-IV line in FIG. 3; FIG. 5 is a cross-sectional view of the barrel body and a light guiding member along a V-V line in FIG. 3; FIG. 6 is a perspective view enlargingly showing the barrel body in FIG. 3; FIG. 7 is a plan view when the barrel body in FIG. 6 is seen in a VII direction in FIG. 6; and FIG. 8 is a cross-sectional view of the barrel body along a VIII-VIII line in FIG. 7.

Figure 9:
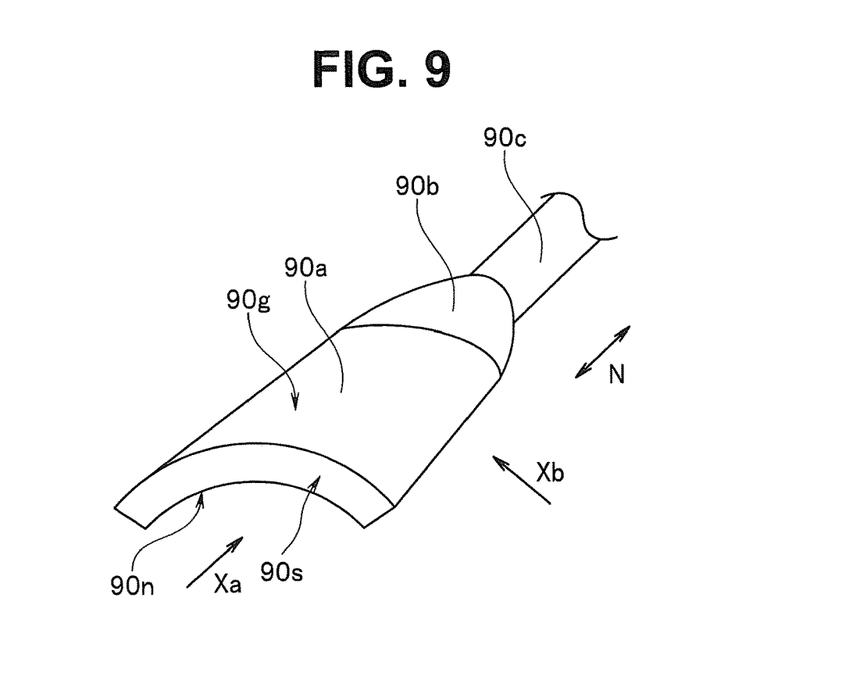
FIG. 9 is a partial perspective view enlargingly showing the light guiding member in FIG. 3.
Figure 10:
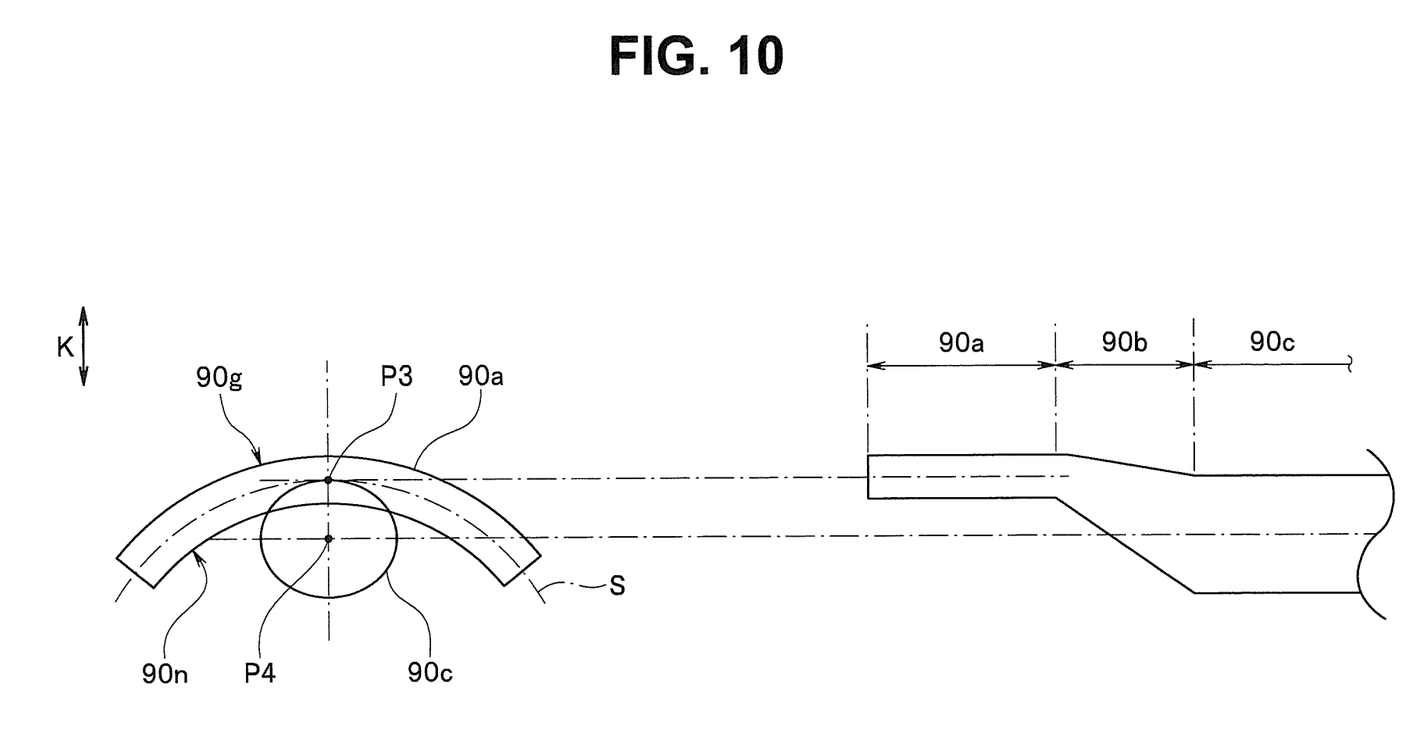
FIG. 10 is a diagram showing a front view of the light guiding member in FIG. 9 when the light guiding member is seen in an Xa direction in FIG. 9 and a side view of the light guiding member in FIG. 9 when the light guiding member is seen in an Xb direction in FIG. 9, side by side.

Furthermore, FIG. 9 is a partial perspective view enlargingly showing the light guiding member in FIG. 3; and FIG. 10 is a diagram showing a front view of the light guiding member in FIG. 9 when the light guiding member is seen in an Xa direction in FIG. 9 and a side view of the light guiding member in FIG. 9 when the light guiding member is seen in an Xb direction in FIG. 9, side by side.

As shown in FIG. 2, on a distal end face 6s of the distal end portion 6, a projecting portion 40 columnarly projecting forward in the longitudinal axis direction N (hereinafter merely referred to as forward) from the distal end face 6s is provided.

The projecting portion 40 is configured with a first projecting portion 11 and a second projecting portion 18 provided adjoining the first projecting portion 11 in a radial direction K of the insertion portion 4 in an intersection direction intersecting the longitudinal axis direction N. (Hereinafter, reference symbol K is also attached to the intersection direction.)

As shown in FIGS. 2 and 3, an observation optical system configured to observe a subject illuminated by illumination lenses 15, 16 and 24 described later is provided in the first projecting portion 11.

More specifically, in the first projecting portion 11, a front observation lens 12 which is a first observation optical system configured to observe an area in the longitudinal axis direction N to acquire a front object image is provided, being exposed on a distal end face 11s of the first projecting portion 11.

Note that the front object image is an object image of an object located in the longitudinal axis direction N including a forward direction ahead of the distal end face 11s.

In the first projecting portion 11, a surrounding observation lens 13 is provided which is a second observation optical system exposed in a circumferential shape along an outer circumferential face 11g of the first projecting portion 11 and configured to observe an area including the surrounding direction which is an intersection direction K and acquire a side object image, the second observation optical system having a shape at least including a partial annular shape. Hereinafter, the partial annular shape is assumed to be a shape at least including a part of an annular shape such as a ring, both ends of which are not closed.

Note that, in the first projecting portion 11, the surrounding observation lens 13 is located more rearward than the front observation lens 12 in the longitudinal axis direction N (hereinafter merely referred to as rearward) as shown in FIG. 3.

The side object image is an object image of an object located in the surrounding direction. Note that reference symbol K is also attached to the surrounding direction.

In the distal end portion 6, a rear lens group 14, which is an observation optical system configured with a plurality of lenses, is provided more rearward than the surrounding observation lens 13, and an image pickup portion 20 such as a CCD is provided at an image forming position of the rear lens group 14 as shown in FIG. 3.

The image pickup portion 20 picks up an image of a front object acquired by the front observation lens 12 and an image of an object in the surrounding direction K acquired by the surrounding observation lens 13.

Note that since a configuration for incidence of light of the front object onto the image pickup portion 20 via the front observation lens 12, the surrounding observation lens 13 and the rear lens group 14 and a configuration for incidence of light of the object in the surrounding direction K via the surrounding observation lens 13 and the rear lens group 14 are well known, detailed description of the configurations will be omitted.

The front object image and the side object image picked up by the image pickup portion 20 are image-processed, and, after that, display image signals are generated and outputted to the monitor 36.

As a result, the front object image is displayed in a substantially circular shape in a center of the monitor 36, and the side object image is displayed in a substantially C shape, surrounding an outer circumference of the front object image.

Note that it is because a part of a field of view of the surrounding observation lens 13 is blocked by the second projecting portion 18 that the side object image is displayed not in a ring shape but in a C shape, that is, a non-displayed area is generated on the monitor 36.

As shown in FIGS. 2 and 3, on the outer circumferential face 11g of the first projecting portion 11, the illumination lens 24 which is a light emitting member configured to supply illumination light in the surrounding direction K is continuously provided in a circumferential direction C around a longitudinal axis in a substantially annular shape excluding the second projecting portion 18, behind the surrounding observation lens 13. Note that a detailed configuration of the illumination lens 24 will be described later.

The second projecting portion 18 constitutes a cover 60 covering the distal end face 6s and a distal end side of an outer circumferential face 6g of the distal end portion 6 excluding the first projecting portion 11, the illumination lens 16 described later and the suction port 17.

Therefore, the second projecting portion 18 is a body separate from the distal end portion 6 and the first projecting portion 11 and is attached to the distal end portion 6. Note that the second projecting portion 18 may be formed integrally with the distal end portion 6 and the first projecting portion 11.

On a distal end face 18s of the second projecting portion 18, the illumination lens 15 configured to supply illumination light ahead of the distal end face 18s is provided. On the distal end face 18s, a front-view type observation window nozzle portion 19 configured to supply fluid toward the front observation lens 12 and the illumination lens 15 is provided.

On an outer circumferential face 18g of the second projecting portion 18, for example, two surrounding observation window nozzles 22 configured to supply fluid toward the surrounding observation lens 13 are provided, facing each other in the radial direction K. Note that the number of surrounding observation window nozzles 22 is not limited to two.

Furthermore, on the distal end face 6s of the distal end portion 6, a distal end of the suction channel configured to suck liquid in a subject is opened as the suction port 17.

On the distal end face 6s, the illumination lens 16 configured to supply illumination light ahead of the distal end face 6s is provided.

Here, as shown in FIGS. 3 and 4, a main part of an illumination unit for endoscope L configured to supply illumination light in the surrounding direction K via the illumination lens 24 is configured with the illumination lens 24 described above, the light guides 90 and 90', which are light guiding members, each of which is configured, for example, as one bundle obtained by bundling a plurality of fibers, and a barrel body 50 which is a positioning member.

The illumination lens 24 is formed in a substantially annular shape in the circumferential direction C as described above such that the second projecting portion 18 is excluded. By the illumination lens 24 being continuously formed in a substantially annular shape in the circumferential direction C without being interrupted, it is possible to uniformly supply illumination light in the surrounding direction K without irregularity.

Note that, in the present embodiment, a case where two light guides (90 and 90') are provided is shown as an example. It is assumed that what is shown as the light guide 90 is also applicable to the light guide 90'. Of course, more than two light guides may be provided.

As shown in FIGS. 3 and 4, a main part of the illumination lens 24 is configured with a light guiding layer 81 which is a first layer and a diffusing layer 82 which is a second layer.

The light guiding layer 81 has each of an end face 81t provided in the radial direction K and an outer circumference portion 81g provided in the circumferential direction C around the longitudinal axis, and the light guiding layer 81 is configured to diffuse illumination light incident onto the end face 81t inside and is configured, for example, with transparent resin.

As shown in FIG. 4, an inner circumference 81n side and the outer circumference portion 81g side of the light guiding layer 81 in the radial direction K are formed in circular arcs in the circumferential direction C, that is, shapes at least including partial annular shapes.

The diffusing layer 82 is arranged on an outer layer side of the outer circumference portion 81g of the light guiding layer 81 in the radial direction K and is configured to diffuse illumination light diffused by the light guiding layer 81 in the radial direction K. The diffusing layer 82 is formed, being integrated with the light guiding layer 81 by two-color molding or the like by dispersed particles such as glass beads being mixed with resin so that a part of an outer surface 82g forms a shape at least including a partial annular shape in the circumferential direction C.

The light guide 90 guides illumination light to the illumination lens 24, and a main part is configured having a proximal end face 90k onto which illumination light from a light source 500 is incident and a distal end face 90s as shown in FIG. 3. The distal end face 90s faces the end face 81t of the light guiding layer 81 to cause illumination light to be incident onto the light guiding layer 81, and a planar shape when the distal end face 90s is seen from a front is formed in a shape including an oval shape obtained by extending a circle in the circumferential direction C as shown in FIGS. 5, 9 and 10.

More specifically, as shown in FIGS. 9 and 10, an inner circumference 90n side and an outer circumference 90g side of the light guide 90 are formed in circular arcs, and a main part is configured having a rigid circular arc portion 90a having the distal end face 90s, a cross-section of the circular arc portion 90a in the radial direction K being formed in an oval shape, a flexible portion 90c having the proximal end face 90k, a cross-section of the flexible portion 90c in the radial direction K being formed in a circular shape, and a rigid shape transition portion 90b connecting the circular arc portion 90a and the flexible portion 90c in the longitudinal axis direction N, the rigid shape transition portion 90b being a portion where a cross-sectional shape changes.

Note that, as the oval shape, an ellipse, an egg shape, a cocoon shape, a rounded rectangle and an elongated circular shape corresponding to a shape obtained by connecting an end point of one circular arc between two circular arcs obtained by dividing one circle into halves and an end point of the other circular arc with two lines are included.

A reason why the cross-section of the circular arc portion 90a is formed in an oval shape is that, if the cross-section is formed in a circular shape, an outer diameter of the distal end portion 6 increases because a distal end side of the light guide 90 is arranged around the rear lens group 14 as described above. In other words, the reason is that, if the cross-section is formed in an oval shape that is thinner in the radial direction K than a circular shape, increase in the diameter of the distal end portion 6 can be prevented.

The flexible portion 90c is inserted in the bending portion 7 and the flexible tube portion 8 of the insertion portion 4, the operation portion 3, the universal cord 5 and the connector 32, and is configured with a plurality of light guide fibers inserted in an elastic tube.

Note that the light guide 190, the flexible portion 90c of the light guide 90 and a flexible portion of the light guide 90' branch in the connector 32.

A purpose of the flexible portion 90c being configured to be flexible is for the flexible portion 90c to follow movement of the insertion portion 4 and the universal cord 5.

Not only the circular arc portion 90a but a section of the flexible portion 90c is not formed in an oval shape. It is because it is difficult to faun the flexible portion 90c elongated in the longitudinal axis direction N by partially changing rigidity of the light guide 90, maintaining a section in an oval shape.

The illumination lens 24 is provided on the barrel body 50 provided on outer circumferences of a lens barrel 210 configured to hold the rear lens group 14 and a device barrel 220 fitted to an outer circumference on a proximal end side of the lens barrel 210 and configured to hold the image pickup portion 20.

The barrel body 50 positions the distal end sides of the illumination lens 24 and the light guides 90 and 90' in the radial direction K so that all the distal end faces 90s, 90s' (90s' not shown) of the light guides 90 and 90' face the end face 81t of the light guiding layer 81.

As shown in FIGS. 3, 6 and 7, a main part of the barrel body 50 is configured, being provided with a body portion 50b having a space inside where the lens barrel 210 and the device barrel 220 are provided and a cylindrical projecting portion 50t formed to project forward from a distal end face 50s of the body portion 50b, and having a space inside where the lens barrel 210 is provided.

In the body portion 50b, arrangement holes 50h and 50h' where the distal end sides of the light guides 90 and 90', more specifically, the circular arc portions 90a, 90a' (90a' not shown) are arranged are formed to pass through the body portion 50*b* in the longitudinal axis direction N.

An external shape of the arrangement holes 50*h* and 50*h*' is formed to correspond to an external shape of the circular arc portions.

In other words, radiuses of an outer circumference and an inner circumference of the arrangement holes 50*h* and 50*h*' are set to substantially correspond to a radius Rb2 of the outer circumference of the distal end faces of the circular arc portions 90*a*, 90*a*' (90*a*' not shown) and a radius Rb1 of the inner circumference of the distal end faces 90*s*, 90*s*' (90*s*' not shown), and a cross-sectional shape and a plane shape of an external shape are formed in the oval shape described above.

Note that each of the arrangement holes 50*h* and 50*h*' is not limited to an oval shape formed by one hole but may be formed in an oval shape by an aggregate of small circles.

As shown in FIGS. 3, 4 and 8, the cylindrical projecting portion 50*t* is such that the illumination lens 24 described above is arranged on a substantially annular outer circumferential face 50*tg* in a substantially annular shape in the circumferential direction C, and the cylindrical projecting portion 50*t* is formed so that a central axis P corresponds to a central axis P of the arrangement holes 50*h* and 50*h*' as shown in FIG. 5.

Note that, hereinafter, it is assumed that what is referred to as the arrangement hole 50*h* is applied to the arrangement hole 50*h*'.

Here, as shown in FIGS. 4 and 5, the radius Rb1 of the inner circumference of the distal end face 90*s* of the circular arc portion 90*a* is set to be equal to or larger than a radius Ra1 of an inner circumference of the light guiding layer 81 (Ra1≤Rb1). Note that a radius of an outer circumference of the outer circumferential face 50*tg* is almost the same as the radius Ra1 of the inner circumference of the light guiding layer 81.

The radius Rb2 of the outer circumference of the distal end face 90*s* of the circular arc portion 90*a* is set to be equal to or smaller than a radius Ra2 of an outer circumference of the light guiding layer 81 (Ra2≥Rb2).

As shown in FIGS. 4 and 5, the barrel body 50 positions the illumination lens 24 and the light guide 90 using the outer circumferential face 50*tg* and the arrangement hole 50*h* so that the central axis P of the circular arc of the distal end face 90*s* of the circular arc portion 90*a* and the central axis P of the light guiding layer 81 in the radial direction K are coaxial or substantially coaxial with each other.

Thereby, when the illumination lens 24 is arranged on the outer circumferential face 50*tg*, and the circular arc portions 90*a*, 90*a*' (90*a*' not shown) are arranged in the arrangement holes 50*h* and 50*h*', all the distal end faces 90*s*, 90*s*' (90*s*' not shown) face the end face 81*t* of the light guiding layer 81. In other words, all illumination light radiated from the distal end faces is incident onto the light guiding layer 81.

Here, "all" is intended to mean that an end face of each of the number of light guides required to emit a required amount of light (required for the amount of light not to decrease) certainly faces the end face 81*t* of the light guiding layer 81, and, for example, it is not excluded that, while a state in which the required amount of light can be emitted is maintained, some of all the number of light guides are intentionally caused to be in a state of not facing the end face 81*t* of the light guiding layer 81.

Here, when the circular arc portion 90*a* is provided being fitted in the arrangement hole 50*h*, the light guide 90 is formed in such a shape that a central axis P4 of the flexible portion 90*c* is located nearer to a center of the distal end portion 6 in the radial direction K than a central axis P3 of the circular arc portion 90*a*, by the shape transition portion 90*b* as shown in FIG. 10.

Note that the central axis P3 of the circular arc portion 90*a* refers to a point at which a line extended from the central axis P4 toward the circular arc portion 90*a* side in the radial direction K intersects a bisector S of the circular arc portion 90*a* in the radial direction K.

As shown in FIG. 3, the rigid shape transition portion 90*b* of the light guide 90 is located on a more proximal end side than the rear lens group 14 in the distal end portion 6.

Thereby, it becomes possible to arrange the flexible portion 90*c* located on a more proximal end side than the rear lens group 14 and having a circular section, causing the flexible portion 90*c* to be offset from the circular arc portion 90*a*, near to a center of the insertion portion 4 in the radial direction K. Therefore, it is possible to reduce a diameter of the insertion portion 4 without decreasing the number of light guide fibers constituting the light guide 90.

Note that other components of the illumination unit for endoscope L are similar to components of a conventional illumination unit for endoscope, description of the other components will be omitted.

Thus, in the present embodiment, it has been shown that the barrel body 50 positions the illumination lens 24 and the circular arc portions 90*a*, 90*a*' (90*a*' not shown) so that all the distal end faces 90*s*, 90*s*' (90*s*' not shown) of the light guides 90 and 90' face the end face 81*t* of the light guiding layer 81.

More specifically, the substantially annular-shaped illumination lens 24 is provided on the substantially annular-shaped outer circumferential face 50*tg* of the cylindrical projecting portion 50*t* of the barrel body 50; the radius Rb1 of the inner circumference of the distal end face 90*s* of the circular arc portion 90*a* arranged in the arrangement hole 50*h* fondled in the body portion 50*b* is set to be equal to or larger than the radius Ra1 of the inner circumference of the light guiding layer 81 (Ra1≤Rb1); the radius Rb2 of the outer circumference of the distal end face 90*s* of the circular arc portion 90*a* is set to be equal to or smaller than the radius Ra2 of the outer circumference of the light guiding layer 81 (Ra2≥Rb2); and the radiuses of the outer circumference and inner circumference of the arrangement hole 50*h* are set almost the same as the radius Rb2 of the outer circumference of the distal end face 90*s* of the circular arc portion 90*a* and the radius Rb1 of the inner circumference of the distal end face 90*s*. It has been shown that, thereby, the barrel body 50 positions the circular arc portion 90*a* arranged in the arrangement hole 50*h* relative to the illumination lens 24 arranged on the outer circumferential face 50*tg* in the radial direction K.

From the above, only by causing the circular arc portions 90*a*, 90*a*' (90*a*' not shown) to be fitted and arranged in the arrangement holes 50*h* and 50*h*', all of the distal end faces 90*s*, 90*s*' (90*s*' not shown) certainly face the end face 81*t* of the light guiding layer 81 without being displaced in the radial direction K.

Therefore, it is possible to cause illumination light to be efficiently incident onto the light guiding layer 81 from the distal end faces 90*s*, 90*s*' (90*s*' not shown) without a light quantity loss.

Further, since the illumination lens 24 is formed in a substantially annular shape in the circumferential direction C without being interrupted, it is possible to supply illumination light incident onto the light guiding layer 81 to a wide range in the surrounding direction K from the diffusing layer 82 without irregularity.

From the above, it is possible to provide the illumination unit for endoscope L in a configuration in which, since it is possible to easily cause all the distal end faces 90s, 90s' (90s' not shown) of the light guides 90 and 90' to face the light guiding layer 81, it is possible to supply illumination light to a wide range in the surrounding direction K without irregularity, and the endoscope 2.

Figure 11:
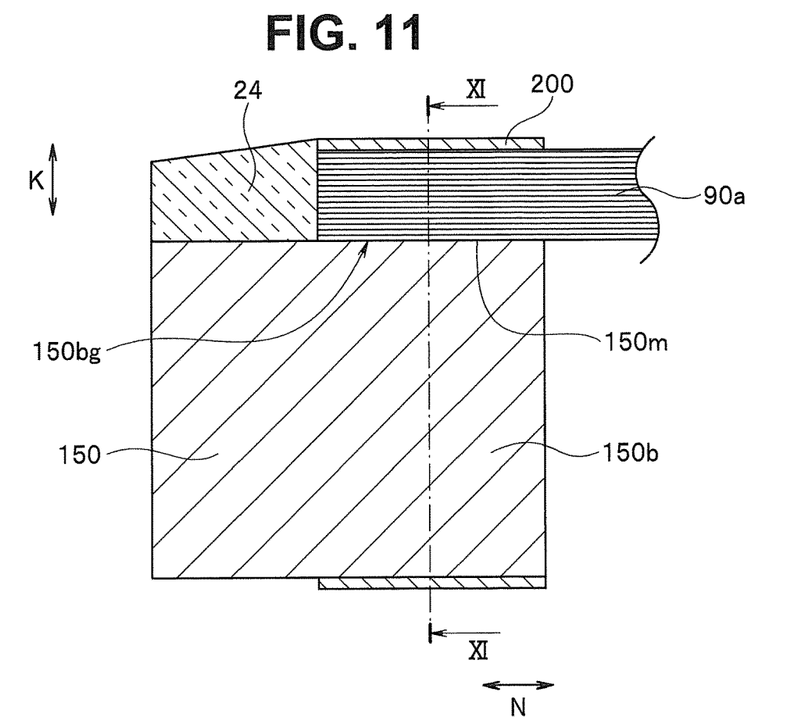
FIG. 11 is a partial cross-sectional diagram showing a modification of a shape of the barrel body in FIG. 6.

Note that a modification will be shown below with the use in FIGS. 11 and 12. FIG. 11 is a partial cross-sectional diagram showing a modification of the shape of the barrel body in FIG. 6; and FIG. 12 is a cross-sectional view of the barrel body, the cylindrical member and the light guides along an XI-XI line in FIG. 11.

In the embodiment described above, the barrel body 50, which is a positioning member, has the arrangement holes 50h and 50h' in the longitudinal axis direction N, and the circular arc portions 90a, 90a' (90a' not shown) of the light guides 90 and 90' are fitted into the arrangement holes 50h and 50h'. It has been shown that positioning of the distal end faces 90s, 90s' (90s' not shown) relative to the light guiding layer 81 provided on the outer circumferential face 50tg in the radial direction K is performed thereby.

Figure 12:
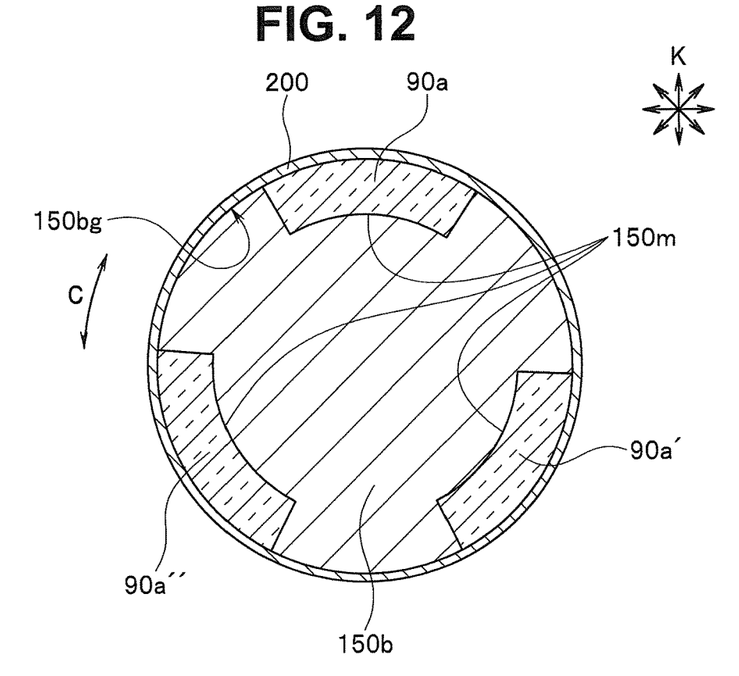
FIG. 12 is a cross-sectional view of the barrel body, a cylindrical member and light guides along an XI-XI line in FIG. 11.

Regardless of the above, as shown in FIGS. 11 and 12, a barrel body 150, which is a positioning member, may be provided with an arrangement groove 150m which is formed on an outer circumferential face 150bg of a body portion 150b of the barrel body 150 in the longitudinal axis direction N and in which the circular arc portion 90a is arranged, and a cylindrical member 200 configured to block the circular arc portion 90a arranged in the arrangement groove 150m between the cylindrical member 200 and the body portion 150b in the radial direction K by covering the outer circumferential face 150bg of the body portion 150b of the barrel body 150 and may perform positioning of the distal end face 90s relative to the light guiding layer 81 in the radial direction K by the circular arc portion 90a being arranged in the arrangement groove 150m and being blocked by the cylindrical member 200.

According to such a configuration, processing of a barrel body becomes easier by forming grooves on the barrel body than forming holes like the embodiment described above, and a barrel body structure can be simplified. Other effects are the same as the effects of the embodiment described above.

Note that, in FIG. 12, a case is shown where three arrangement grooves 150m are formed on the body portion 150b, and the arrangement grooves 150m are provided with circular arc portions 90a, 90a' and 90a'', respectively, as an example. In other words, a case where there are three light guides is shown as an example. Regardless of the above, in the configuration shown in FIGS. 11 and 12, the number of light guides is also not limited to three.

Further, though a case where a plurality of object images are displayed on one monitor has been shown as an example in the embodiment described above, it goes without saying that, regardless of the above, object images may be displayed on a plurality of monitors.

Furthermore, the endoscope 2 in the embodiment described above is, of course, not limited to medical use but is applicable to industrial use.

What is claimed is:

1. An illumination unit for endoscope, comprising:
   a light emitting member provided on a distal end side of an insertion portion of an endoscope in a longitudinal axis direction, the light emitting member including a first material and a second material, the first material including an end face provided in an intersection direction intersecting the longitudinal axis direction and an outer circumference portion provided in a circumferential direction around a longitudinal axis, the first material being configured to diffuse illumination light incident onto the end face inside, and the second material being arranged on an outer layer side in the intersection direction with respect to the outer circumference portion of the first material and configured to cause the illumination light diffused by the first material to be diffused in the intersection direction;
   light guides configured to guide the illumination light to the light emitting member, each of the light guides including a proximal end face onto which the illumination light from a light source is incident, and a distal end face facing the end face of the first material to cause the illumination light to be incident onto the first material and having at least a portion having an oval shape obtained by extending a circle in the circumferential direction; and
   a positioning member configured to position the light emitting member and the light guides in a radial direction of the insertion portion in the intersection direction so that all the distal end faces of the light guides face the end face of the first material; wherein
   the positioning member having a barrel body on which arrangement grooves are formed in the longitudinal axis direction such that the positioning member inwardly positions the light guides in the radial direction by distal end sides of the light guides in the longitudinal axis direction being arranged in the arrangement grooves, and a cylindrical member configured to outwardly position the light guides in the radial direction by covering an outer circumference of the barrel body in the intersection direction to block the distal end sides of the light guides arranged in the arrangement grooves, between the cylindrical member and the barrel body in the intersection direction.

2. The illumination unit for endoscope according to claim 1, wherein the light emitting member is formed in a shape such that a part of an outer surface of the second material at least includes a partial annular shape.

3. The illumination unit for endoscope according to claim 2, wherein
   inner circumference sides and outer circumference sides of the first material and the distal end faces of the light guides in the radial direction are formed in circular arcs;
   a radius of the inner circumferences of the distal end faces of the light guides is equal to or larger than a radius of the inner circumference of the first material; and
   a radius of the outer circumferences of the distal end faces of the light guides is equal to or smaller than a radius of the outer circumference of the first material.

4. The illumination unit for endoscope according to claim 2, wherein
   inner circumference sides and outer circumference sides of the first material and the distal end faces of the light guides in the radial direction are formed in circular arcs; and
   the positioning member positions the light emitting member and the light guides so that a central axis of the circular arcs of the distal end faces of the light guides and a central axis of the first material in the intersection direction are coaxial or substantially coaxial with each other.

5. The illumination unit for endoscope according to claim 4, wherein each of the light guides is formed in a shape such that a central axis of the proximal end face of each of the light guides is located nearer to a center of the insertion portion in the intersection direction than the central axis of the distal end face of each of the light guides.

6. The illumination unit for endoscope according to claim 1, wherein, as at least the oval shape of the distal end face of each of the light guides, an ellipse, a rounded rectangle and an elongated circular shape corresponding to a shape obtained by connecting an end point of one circular arc between two circular arcs obtained by dividing one circle into halves and an end point of the other circular arc with two lines are included.

7. The illumination unit for endoscope according to claim 6, further comprising an observation optical system disposed on the distal end side of the insertion portion of the endoscope in the longitudinal axis direction, the observation optical system being configured to observe a subject illuminated by the illumination light; and wherein a part of each of the light guides where a cross-sectional shape of the distal end face changes to a cross sectional shape of the proximal end face is located on a more proximal end side in the longitudinal axis direction on the insertion portion than a part where the observation optical system is provided.

8. The illumination unit for endoscope according to claim 7, wherein the observation optical system comprises:
a first observation optical system configured to observe a direction including the longitudinal axis direction; and
a second observation optical system configured to observe a direction including the intersection direction and having a shape at least including a partial annular shape.

9. The illumination unit for endoscope according to claim 1, wherein proximal end sides of the light guides in the longitudinal axis direction are configured to be more flexible than the distal end sides in the longitudinal axis direction having the distal end faces.

10. An endoscope comprising the illumination unit for endoscope according to claim 1.

* * * * *